United States Patent [19]

Teitz

[11] Patent Number: 4,927,843
[45] Date of Patent: May 22, 1990

[54] ANTIVIRAL COMPOSITIONS

[75] Inventor: Yael Teitz, Ramat-Gan, Israel

[73] Assignee: Ramot Univ. Authority for Applied Res. & Devp. Ltd., Tel-Aviv, Israel

[21] Appl. No.: 167,507

[22] Filed: Mar. 14, 1988

Related U.S. Application Data

[63] Continuation-in-part of Ser. No. 948,415, Dec. 31, 1986, abandoned.

[30] Foreign Application Priority Data

Jan. 1, 1986 [IL] Israel ......................................... 77496

[51] Int. Cl.$^5$ ............................................. A61K 31/40
[52] U.S. Cl. .................................................. 514/418
[58] Field of Search .......................................... 514/418

[56] References Cited

U.S. PATENT DOCUMENTS 3,253,991 5/1966 Bauer et al. ........................... 514/418

FOREIGN PATENT DOCUMENTS 898855 6/1962 United Kingdom ................. 514/418

OTHER PUBLICATIONS

Chemical Abstracts 92:174238y (1980).
Chemical Abstracts 102:89706e(1985) Abstraction.
Chemical Abstracts 103: 153403d (1985) Abstraction.
Activiral Res. 1985, Ronen et al. 5(4) 249–54.
Bauer, D. (ed), "Chemotherapy of Virus Diseases", vol. 1 (1972), published by Pergamon Press Oxford in International Encyclopedia of Pharmacology and Therapeutics pp. 35 & 36.
Zinsser Microbiology, 17th Ed., published by Appleton–Century–Crofts, New York, (1980), pp. only 3 pages of table 62-4.

*Primary Examiner*—Jerome D. Goldberg
*Attorney, Agent, or Firm*—Browdy and Neimark

[57] ABSTRACT

The invention relates to novel pharmaceutical compositions which are effective against a wide spectrum of viruses belonging to the Retroviridae family. The active ingredient of the compositions is a thiosemicarbazone compound as herein defined. The compounds are similar to the well-known compound M-IBT (methyl isatin-$\beta$-thiosemicarbazone) which has been widely used against smallpox. Contrary to the compounds used according to the present invention, one of which is novel by itself, M-IBT is not effective against viruses of the Retroviridae against which the novel compositions are active.

7 Claims, No Drawings

4,927,843

ANTIVIRAL COMPOSITIONS

STATUS OF THE PATENT APPLICATION

The present application is a continuation in part application (CIP) of U.S. patent application No. 948,415 of 31 Dec. 1986, now abandoned.

FIELD OF THE INVENTION

The invention relates to pharmaceutical compositions which are of value in human and veterinary medicine for the treatment of diseases caused by viruses belonging to the Retroviridae family. The novel compositions are of value for the treatment of a wide range of diseases caused by such viruses, such as acute and chronic leukemia, carcinoma, sarcoma, acquired immune deficiency syndrome and the like. The active ingredient of the compositions is a specific isatine thiosemicarbazone derivative. Some of these are known as such, while one is novel. Their use against viruses of the Retroviridae is novel.

BACKGROUND OF INVENTION

Certain thiosemicarbazones—especially substituted isatine 3-thiosemicarbazones—have an antiviral activity. These have been reviewed by Bauer [Bauer, D. (ed). In: Chemotherapy of Viral Diseases: Thiosemicarbazones (1972) Vol. 1, Pergaman Press, Oxford (5) in U.K. Patent No. 975357, 1964 to Wellcome Foundation, which relates to N-methylisatine 3-thiosemicarbazone (M-IBT)—commercially known as Methisazone or Marborane), and which is one of the few clinically effective synthetic antiviral drugs acting by the inhibition of replication of DNA containing pox viruses. It has been established that N-methylisatin-$\beta$-4',4'-diethylthiosemicarbazone (in the following M-IBDET) inhibits the production of Moloney leukemia virus (1-3). This does not imply, and does not permit any prediction, as regards the possible activity of this type of compounds against animal and human diseases caused by other retroviruses. As a matter of fact, the well-known Marborane has been tested by us and has been found to be ineffective against the viruses of the Retroviridae against which the compositions of the invention are effective.

SUMMARY OF THE INVENTION

The present invention relates to pharmaceutical compositions for the alleviation of symptoms of and for treatment of a variety of human and animal diseases caused by viruses of the Retroviridae family. The compositions of the invention are of value in the treatment of a variety of viral diseases such as acute and chronic leukemia, carcinoma and sarcoma as well as acquired immune deficiency syndrome (AIDS). The active ingredients of the pharmaceutical compositions of the invention are of the formula

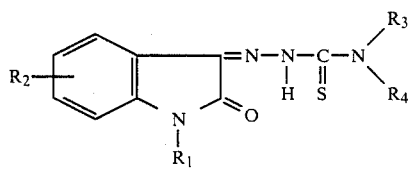

where $R_1$ represents an alkyl, alkoxy or alkenyl radical, having not more than 6 carbon atoms each;

$R_2$ is an optional substituent representing a halogen atom or an alkyl or alkoxy radical having no more than 6 carbon atoms;

$R_3$ and $R_4$, are the same or different and represent a cycloalkyl, a straight or a branched alkyl radical of no more than 6 caron atoms, or alkenyl radical having no more than 6 carbon atoms; or $N=R_3R_4$ is a heterocyclic group like pyrrolidyl, piperidyl, morpholynyl or $H=$alkylhexahydropirazinyl.

A compound of choice is the known compound N-methylisatine 3-thiosemicarbazone wherein $R_1$ is methyl and $R_3$ and $R_4$ are hydrogen.

The most promising compounds in this series seem to be the following:

(1) 1-methylisatin-$\beta$-4':4'-diethylthiosemicarbazone (I, $R_1=CH_3$—, $R_2=H$, $R_3=R_4=C_2H_5$—)-M-IBDET.

(2) 1-allylisatin-$\beta$-4':4'-dimethylthiosemicarbazone (I, $R_1=CH_2=CH-CH_2$—; $R_2=H$; $R_3=R_4=CH_3$—). A-IBDMT.

(3) 1-allylisatin-$\beta$-4':4'-diethylthiosemicarbazone (I, $R_1=CH_2=CH-CH_2$, $R_2=H-R_3=R_4=C_2H_5$—) A-IBDET.

The novel compositions are formulated to pharmaceutical compositions in a conventional manner. The preferred route of administration is the oral one. Other routes can be resorted to as well. The above compounds have been found to be highly effective, at small and non-toxic concentrations, against a wide variety of Retroviridae, as set out in detail hereinafter.

The Retroviridae family includes three sub-families:

1. Oncoviruses—Comprising of the A,B,C,D type RNA tumor viruses, and the $HTLV_I$ and $HTLV_{II}$ viruses.
2. Lentiviruses—Comprising of the Visna Maedi virus Equine infectious anemia virus (EIAV), Caprine arthritis encephalitis virus (CAEV), and human immunodeficiency virus (HIV)—the ethiological agent of AIDS.
3. Spumaviruses—Comprising of foaming viruses. A detailed list of viruses belonging to the Retrovirida family has been published in Fields B. N., (1985) Virology, Raven Press, pp. 237-238.

The Oncoviruses are very abundant in nature and cause, in their natural host (avian, rodent, feline, canine, monkey), sarcoma, carcinoma, leukemia, and lymphoma. In humans, the T-lymphotropic virus I-$HTLV_I$ and $HTLV_{II}$ cause adult T-cell leukemia/lymphoma.

The Lentiviruses include viruses that cause persistent disease in animals and humans.

Visna and Maedi virus cause pneumonia and meningoencephalitis in sheep and goats.

The Caprine arthritis encephalitis virus (CAEV) causes arthritis, pneumonia meningoencephalitis in goats and sheep. The Equine infectious anemia virus (EIAV) causes fever, anemia in horses. The human immunodeficiency virus (HIV), is the ethiological agent of AIDS.

The thiosemicarbazone compounds described in this invention, were found by us to be specific inhibitors of viruses belonging to the Retroviridae family. Results obtained in our laboratory indicate that amounts ranging from 17 $\mu$M to 34 $\mu$M of the thiosemicarbazones suppressed specifically the production of viruses belonging to the Retroviridae family. The extent of inhibition of virus production in the infected cells was 75–85%. This inhibition was confirmed by various parameters of virus assay such as: reverse transcriptase activity, virus infectivity and contents of viral structural proteins. Moreover, it was shown in in-vitro translation system that the translation of Retroviruses m-RNA to viral proteins was specifically inhibited by one of the thiosemicarbazone compounds (4).

Experiments in-vivo indicated that the highest non-lethal dose of the thiosemicarbazones in this invention while injected intraperitonially (ip) to ICR mice 20 g-weight ranged from 50 mg to 100 mg per 1 Kg weight.

One of the few effective previously known antiviral drugs used in human medicine is methylisatine-β-thiosemicarbazone (M-IBT). This drug is effective in the treatment of the pox-virus family. The highest non-lethal dose of M-IBT given (IP) to ICR mice 20 g-weight is in the same range as found for the thiosemicarbazones of this invention, and is: 50 mg M-IBT per 1 Kg-weight of ICR mice.

Administration of the known M-IBT to humans in field trials in India and Pakistan who had contact with smallpox was described in detail. Doses of 40 mg M-IBT per kg of body-weight were given orally for 4 consecutive days with effective results. This invention indicates the potential efficacy of these thiosemicarbazones for use in the treatment of chronic and acute leukemia, carcinoma, sarcoma and AIDS, caused by viruses belonging to the Retroviridae family.

DESCRIPTION OF THE PREFERRED EMBODIMENT

Experimental Results

A. Chemical description of the thiosemicarbazone compounds:

The compounds of this invention are suitably substituted isatin-β-thiosemicarbazones represented by the general formula I

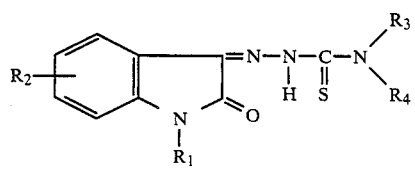

where $R_1$, represents an alkyl, hydroxy or alkenyl radical, having not more than 6 carbon atoms each.

$R_2$—is an optional substituent representing a halogen atom or an alkyl or alkoxy radical having no more than 6 carbon atoms.

$R_3$ and $R_4$—are the same or different and represent a cycloalkyl or a straight or a branched alkyl radical of no more than 6 carbon atoms, or alkenyl radical having no more than 6 carbon atoms; or N-$R_3R_4$ is a heterocyclic group like pyrrolidyl, piperidyl or N-alkylhexahydropirazinyl.

The most promising compounds in this series seem to be the following:

(1) 1-methylisatin-β-4':4'-diethylthiosemicarbazone (I, $R_1$=CH$_3$—, $R_2$=H, $R_3$=$R_4$=C$_2$H$_5$—)-M-IBDET.

(2) 1-allylisatin-β-4':4'-dimethylthiosemicarbazone (I, $R_1$=CH$_2$=CH—CH$_2$—; $R_2$=H; $R_3$=$R_4$=CH$_3$—). A-IBDMT.

(3) 1-allylisatin-β-4':4'-diethylthiosemicarbazone (I, $R_1$=CH$_2$=CH—CH$_2$—, $R_2$=H—$R_3$=$R_4$=C$_2$H$_5$—) A-IBDET.

The procedure of preparation of the compounds M-IBDET and A-IBDET have been described previously by D. J. Bauer and P. W. Sadler (Brit. Pat. 1026401).

The compound: Allylisatin β-4'-4'-dimethylthiosemicarbazone was prepared by us. The preparation is as follows: 1-allylisation (0.34 g) and 4,4-dimethylthiosemicarbazide (0.24 g) in ethanol (2 ml) were refluxed for two hours. The precipitate was recrystallized from isopropanol and melted at 152°–153° C.

B. Procedure of In-vitro and In-vivo Drug Application for Determination of antiviral Activity:

The compounds mentioned above were finely powdered and suspended in sterile manner in the solvent dimethylsulfoxide (DMSO). Stock solutions of 10 mg/ml DMSO were prepared and used for preparation of the various dilutions employed for the in-vitro examinations. Dilutions from stock solution were prepared either in phosphate saline buffer (PBS) pH-7.0 or in growth medium—minimal essential medium (Eagle's MEN).

C. Anti-Oncoviruses Activity of the Thiosemicarbazones.

Our experimental results relate to the inhibition of onco-viruses by the described thiosemicarbazone compounds. These are summarized in Table I, page 9. Different fibroblasts cell-lines, chronically infected with various oncoviruses (see Table 1) were incubated with different concentrations of the thiosemicarbazone compounds. Virus production in drug-treated and untreated cells was followed for 12 hours. Inhibition of virus production was determined by assaying virus reverse transcriptase activity. The inhibition was proportional to drug concentration and time of treatment. Concentrations ranging from 3.4 uM to 34 uM of each of the drugs were tested and found to be effective, giving inhibitions ranging from 20% for the low concentration and an inhibition of 90% in virus production for the 34 uM concentration, after 6 to 9 hours of exposure.

M-IBT was found to be ineffective against these viruses.

TABLE NO. 1

| | ONCOVIRUSES INHIBITED: | |
|---|---|---|
| Origin of Cells | Cell Cultures | Virus |
| Mouse | 3T3/NIH fibroblasts | M-MuLV |
| Mouse | 3T3/NIH fibroblasts | R-MuLV |
| Avian | Chick embryo fibroblasts | RSV |
| Human | human fibroblasts | RD$_{114}$ |
| Human | human fibroblasts | D$_{17}$ |
| Human | human fibroblasts | B$_{95}$ |

The inhibition of the viruses listed in Table I was assayed also by determining virus infectivity. The experimental results showed that exposure of the infected cells to 34 μM of the thiosemicarbazones reduced by 2 logs the infective virus levels after 18 hrs of drug exposure. Analogous runs with M-IBT demonstrated that at such conditions of treatment this compound was not effective.

Effective inhibition by the thiosemicarbazone compounds was also found in another cell system employed for studying retroviruses infections. This system consists lymphocytes chronically infected with various oncoviruses. Thus inhibition of virus growth was shown in two lymphocyte systems: mouse B lymphocytes chronically infected with Abelson Moloney Murine leukemia virus (Ab-MoMuLV) and the human T-lymphocytes chronically infected with HTLV$_1$. 10$^5$ cells per ml were treated with 0.5 µg and with 0.1 µg doses of the above described thiosemicarbazones. Ninety percent of inhibition of virus production was found after exposure of the cells for 24 hours. Virus inhibition was confirmed by the various parameters of virus assay such as virus reverse transcriptase activity, virus structural proteins content, and virus infectivity.

D. Anti-Lentiviruses Activity of the Thiosemicarbazone Compounds:

a. Effect of the drugs against EIAV:

Fibroblast cells of drug origin chronically infected with EIAV were incubated for 2 hrs with concentrations ranging from 17 µM to 34 µM of the described thiosemicarbazone compounds. Subsequently the medium was diluted 1:10 to obtain a final concentration of ranging from 1.7 to 3.4 µM. The cultures were further incubated for 24 hours and virus production was assayed in drug-treated and untreated cells. The extent of inhibition of virus production in the treated cultures was 70–80%. M-IBT was tested and found to be ineffective.

b. Effect of the Drugs against the AIDS Virus—HIV

The thiosemicarbazone compounds were examined for their inhibitory effect on the human immunodeficiency virus—HIV in the following chronically infected cell lines:

H9 cell line—A human established T-cell line chronically infected with HIV;

HuT-78 cell line—A human cell line chronically infected with $ARV_2$ (HIV).

concentrations of $5 \times 10^6$ cells per ml were incubated with 17–34 µM of the different thiosemicarbazones. Virus production was assayed in the drug-treated and untreated cells after 7 hrs of exposure. An 85% inhibition of virus production was found in the drug-treated cultures as compared to control untreated cultures. Virus production was determined by assaying various virus parameters such as reverse transcriptase activity, plaque forming units (PFU) and viral structtural protein content.

The compounds were also tested by employing a different way of treatment of the HIV infected cultures: $5 \times 10^6$ infected cells were incubated with 17–34 µM of the drug for 2 hrs. Subsequently a dilution of 1:10 of the medium was performed to final concentration of 1.7–3.4 µM of the drug. The cultures were further incubated for 24 hrs in diluted medium and virus production was assayed. The extent of inhibition of HIV production achieved by the described treatment was 75–85%. M-IBT was evaluated in a similar manner. No inhibition could be detected.

E. Experimental Results in Animals:

a. Drug Application for Animal Infections:

The above mentioned thiosemicarbazone compounds were finally powdered and suspended in dimethylsulfoxid (DMSO)-(Merck) to get stock solutions of 10 mg/ml. Stock solutions were diluted to a final volume of 0.25 ml DMSO to obtain the following concentrations: 2,5 mg, 2 mg; 1.5 L mg, 1 mg, in 0.25 ml final volume.

These concentrations were prepared from the following thiosemicarbazone compounds:

Methylisatin-β-thiosemicarbazone-M-IBT
Methylisatin-β-4':4'-diethylthiosemicarbazone-M-IBDET;
Allylisatin-β-4':4:-diethylthiosemicarbazone-A-IBDET;
Allylisatin-β-4':4'-dimethylthiosemicabazone-A-IDBMT b. Toxicity to Animals:

Each drug concentration of the 4 thiosemicarbazone derivatives was injected in a sterile manner intraperitonally (iP) to a group of 10 ICR mice, each weighing 20 g. After one injection the mice were followed for the highest non-lethal dose, and for the lethal dose. Results are summarized in Table 2, and Table 3. The results are an average of three separate trials.

TABLE 2:

| The highest non-lethal dose, given ip to ICR Mice | |
|---|---|
| Drug | mg/Kg Weight |
| M - IBT | 50 |
| M - IBDET | 50 |
| A - IBDET | 100 |
| A - IBDMT | 100 |

TABLE 3:

| Lethal Dose - 50 (LD50) given ip to ICR Mice | |
|---|---|
| M - IBT (Marborane) | 125 |
| M - IBDET | 125 |
| A - IBDET | 175 |
| A - IBDMT | 175 |

One of the above described thiosemicarbazone derivatives-M-IBT is known as an antiviral drug which is effective in the treatment of humans against smallpox.

This drug was administered orally to humans in a dosage schedule of 40 mg/kg per day for 4 consecutive days.

This regime of treatment was effective against subjects known to have contact with smallpox.

Antiviral Effect of M-IBDET in Mice against B-lymphoma-induced by Ab-MoMuLV:

One of the three compounds, namely M-IBDET was examined as to its efficacy against the Abelson-Moloney murine leukemia virus (Ab-MoMuLV). Injection of susceptible mice with B-cell lymphocytes infected with Ab-MoMuLV usually results in induction of B-type lymphoma within 3 weeks. Treatment of mice immediately after infection with MoMuLV infected cells with M-IBDET at a daily dose of 2 µg/4 g weight for 10 consecutive days caused a delay of 3 weeks in the appearance of the lymphoma in the drug-treated mice as compared with untreated mice.

As the three compounds according to the present invention are effective both in vitro and in vivo (in cell cultures and against B-lymphoma caused by a retrovirus respectively) and the toxicity of these is similar to that of the known compound M-IBT, which has been used clinically on a large scale against smallpox, it can be assumed that pharmaceutical compositions based on the above three compounds will also be effective in higher mammals and in humans against diseases caused by the above Retroviridae.

I claim:

1. A method for inhibiting the production of human viruses of the Retroviridae family, comprising treating a human infected with said virus with a production inhibiting amount of a compound selected from the group consisting of:

1-methylisatin-beta-4':4'-diethylthiosemicarbazone;
1-allylisatin-beta-4':4'-dimethylthiosemicarbazone; and
1-allylisatin-beta-4':4'-diethylthiosemicarbazone.

2. The method of claim 1, wherein said virus is HTLV$_I$, HTLV$_{II}$, HIV, RD$_{14}$, D$_{17}$ or B-95.

3. The method of claim 1, wherein said virus is HTLV$_I$, HTLV$_{II}$ or HIV.

4. The method of claim 1, wherein said virus is HIV.

5. A method according to claim 1, where the daily dosage is about 20 to 200 mg/kg body weight.

6. The method of claim 1, wherein said treating comprises orally administering said production inhibiting amount of said compound to a patient infected with said virus.

7. The method of claim 6, wherein said virus is HIV.

* * * * *